July 22, 1952 W. M. BEALL Plant Pat. 1,116
ROSE PLANT
Filed May 19, 1951
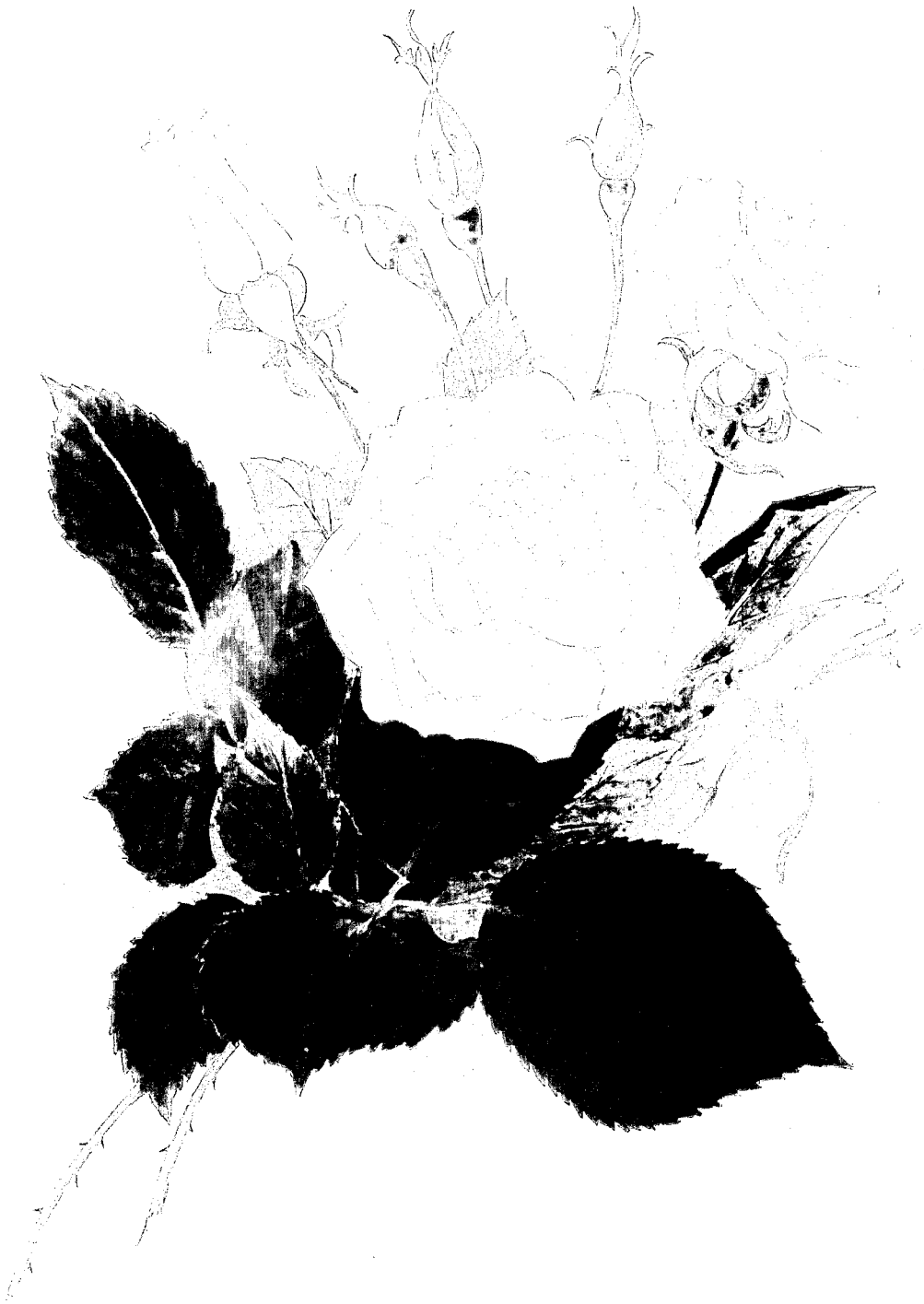
WITNESS
Addison E. Avery
INVENTOR
WALLACE M. BEALL,
By Remington, Remington & Snow,
ATTYS.

Patented July 22, 1952

Plant Pat. 1,116

UNITED STATES PATENT OFFICE 1,116

ROSE PLANT

Wallace M. Beall, Vashon, Wash., assignor to Beall Greenhouse Company, a corporation of Washington Application May 19, 1951, Serial No. 227,223

1 Claim. (Cl. 47—61)

The present invention relates to a new and distinct variety of rose plant of the Floribunda class, which originated as a sport of the variety which is well known by the trade name "Elfe," not patented, discovered in my greenhouse at Vashon, Washington. Reproduction by both budding and grafting has been made at the same location and its characteristics come true to form and are fixed and transmitted through succeeding propagations.

Conspicuous among its characteristics are its long bud compared to "Elfe," its freer blooming habit, better color, vigorous growth, strong stems and abundant foliage which is trouble free.

The accompanying illustration shows the approximately true color of the bloom in various stages of opening.

The colors of this rose in detail and with exactness are as follows, reference being made to Maerz & Paul's Color Dictionary:

| Main color of flowers | Plate | Letter | No. |
|---|---|---|---|
| Lightest petal shade | 1 | E | 2 |
| Blending to— | | | |
| Medium shade | 1 | H | 4 |
| Darkest shade | 1 | A | 6 |
| Base of petals | 17 | K | 1 |
| Foliage: | | | |
| Main leaf color | 23 | L | 9 |
| Underside of leaf | 22 | B | 7 |
| Stem color | 22 | L | 6 |

The following is a detailed description of my new variety:

Parentage: Sport of "Elfe."

Classification: Floribunda. Reproduced asexually from buds and by grafting.

*Flower*

Blooming habit: Continuous; blooms profusely. Is free breaking.

Size: Small like parent. Full blown rose measures substantially 3 inches in diameter.

Borne: Tendency to cluster.

Shape: Has a high center.

Petalage: Number—24 to 26.

*Forms.*—Keystone of arch with rounded side and top and no stalk.

*Color.*—Outer petals, light pink. Inside petals, darker pink. Reverse side of petals, light pink. Base of petals—lemon yellow. This is hidden from the front until flower has fully opened.

*Discoloration.*—None.

*Appearance.*—Satiny and firm.

*Texture.*—Firm.

*Affected by wet or hot weather.*—No.

*Persistence.*—Petals are long-lasting, tending to hang on and dry.

*Disease resistance.*—Average.

*Fragrance.*—Mild.

*Lasting quality.*—On plant—excellent. As a cut flower—excellent.

*Bud*

Size: Small.

Form: Extremely long—does not bullhead like its parent. Is pointed until sepals curl back and petals begin to spread.

Color: When sepals first divide—dark pink with light yellow base. When sepals begin to unfurl—light pink.

Sepals: Long, being twisted together over closed bud and crowned with spatulate appendages.

Receptacle: Pear-shaped, ovoid.

*Size.*—Long and narrow (½ inch x ¼ inch).

*Aspect.*—Smooth and does not split.

Peduncle:

*Length.*—3½ inches.

*Surface.*—Smooth with tiny spines.

*Plant*

Form: Bush.

Height: 4 to 5 feet.

Growth: Very vigorous.

Branching: Yes.

Foliage:

*Quantity.*—Abundant.

*Leaf form.*—Odd-pinnate, groups alternating along main stem and comprising one or more leaflets, odd leaflets at apex and others in pairs.

*Size of leaflet.*—2½ to 3 inches and smaller.

*Texture.*—Leathery and smooth.

*Color.*—Upper side—dark green; under side—light green.

*Shape.*—Ovate-lanceolate with serrated edges.

Thorns: Small and scattered with profuse tiny spines on peduncles and petioles. Color—reddish.

Genital organs: Numerous, compactly arranged and hidden by petal whorls until flowers begin to fade.

*Stamens.*—Length, ⅛ inch. Number, 82. Color, yellow.

*Pollen.*—Color, orange.

*Styles.*—Number, 64; length, ¼ inch.

*Arrangement.*—Circular and curled into a compact mass.

Fruit or hip: Fertile—Yes.

*Shape.*—Ovoid.

*Color at maturity.*—Reddish-green.

This new variety is a very vigorous and healthy grower. It produces an abundance of blooms on sturdy peduncles. The flower opens much like a camellia, its center whorls being tightly coiled over the genital organs which augments this camellia-like appearance. The petals are translucent to rays of light that bring out the distinctively blended light and deep pink coloring of the petals, which gradually shades to a softer pink near the base of the petals where there is a yellow spot. This spot is visible only after the bloom has passed its prime condition and opened flat with the genital organs visible. This characteristic coloring, in combination with the green tones of the foliage, makes this a distinctively novel variety.

The dark pink coloring of the compactly coiled petals of the opening buds last for several days before the bloom is developed, as shown in the drawing, and combines with the lighter pink of the fully opened blooms to produce a very desirable bouquet for commercial use.

Having thus disclosed the invention, I claim:

A new and distinct variety of rose plant, substantially as shown and described, characterized particularly by its vigorous growth; its continuous and free blooming habit; its sturdy stems; long, pointed buds; and the soft pink coloring of its blooms.

WALLACE M. BEALL.

No references cited.